Figure 1:
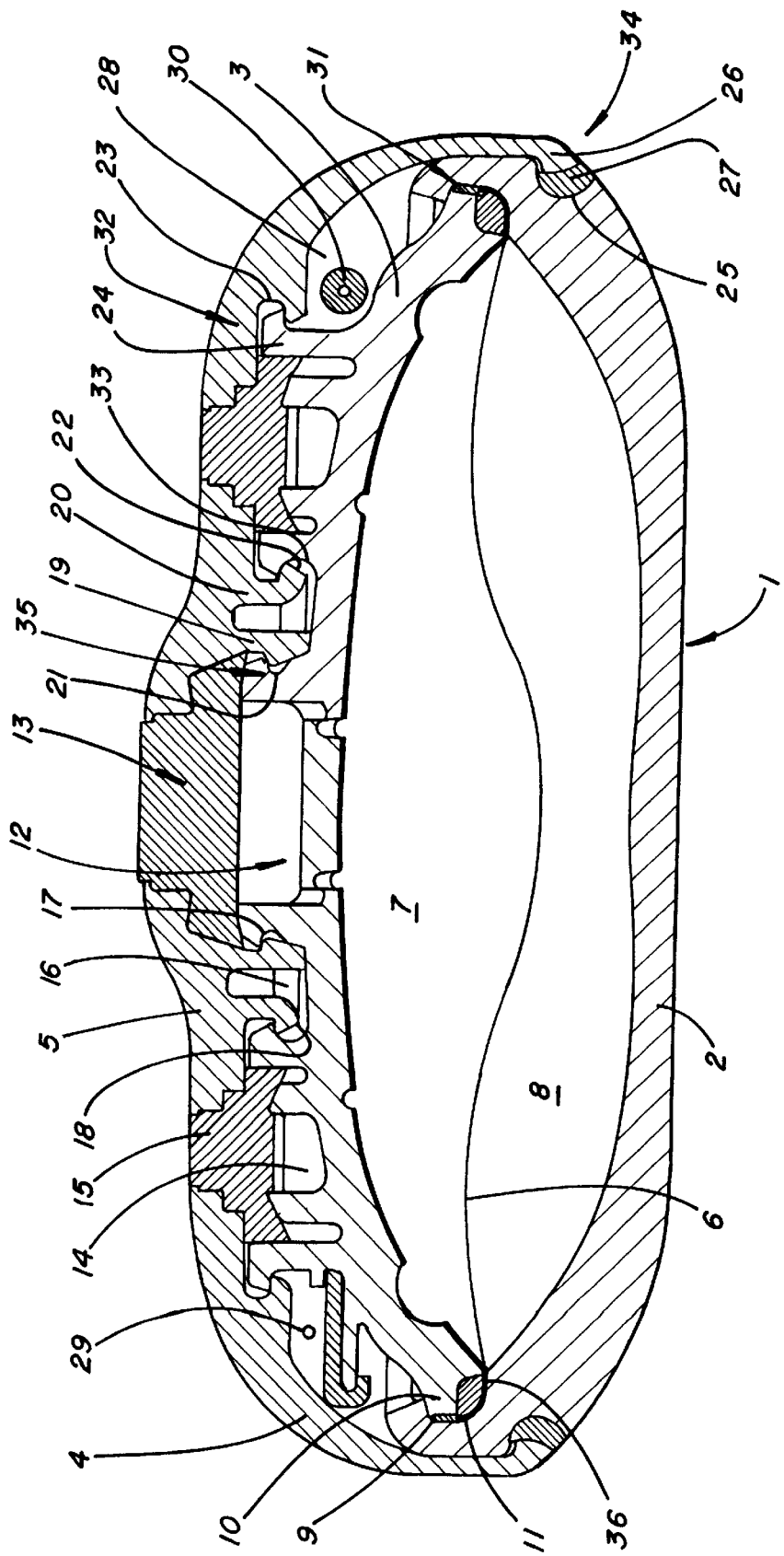

United States Patent
Steinbach et al.

[11] Patent Number: 5,836,915
[45] Date of Patent: Nov. 17, 1998

[54] IMPLANTABLE INFUSION PUMP

[75] Inventors: Bernd Steinbach, Friedberg; Claus Walter, Bad Homburg; Andreas Wild, Friedberg, all of Germany

[73] Assignee: Fresenius AG, Bad Homburg, Germany

[21] Appl. No.: 529,776

[22] Filed: Sep. 18, 1995

[30] Foreign Application Priority Data

Sep. 16, 1994 [DE] Germany ............... 44 32 991.1

[51] Int. Cl.⁶ .................................................. A61M 37/00
[52] U.S. Cl. ............................................ 604/131; 604/140
[58] Field of Search ........................... 604/131, 132, 604/140, 141, 143, 145, 151, 153

[56] References Cited

U.S. PATENT DOCUMENTS

| | | | |
|---|---|---|---|
| 4,969,873 | 11/1990 | Steinbach et al. | 604/145 X |
| 5,102,389 | 4/1992 | Hauser | 604/153 X |
| 5,167,633 | 12/1992 | Mann et al. | 604/141 |
| 5,281,111 | 1/1994 | Plambeck et al. | 604/153 X |
| 5,306,257 | 4/1994 | Zdeb | 604/131 |
| 5,578,005 | 11/1996 | Sancoff et al. | 604/132 X |

Primary Examiner—Manuel Mendez
Attorney, Agent, or Firm—Fulbright & Jaworski L.L.P.

[57] ABSTRACT

The invention concerns an implantable infusion pump for dosed emission of medicines into the human body comprising a pump chamber formed by an upper chamber portion (3) and a lower chamber portion (2), whereby said pump chamber is divided by a flexible membrane (6) into a pressure chamber (8) and a medicine reservoir (7). Refill apertures (12, 14) covered by septa (13, 15) are further provided. The septa (13, 15) are hermetically clamped by holders (4, 5). According to the invention, catch connections are used as main connections (31, 32, 33) and as ancillary connections (34, 35) for the connection of the pump components (2, 3, 4, 5), whereby the main connections (31, 32, 33) substantially support the interior pressure strain generated under normal operating load and the locked ancillary connections (34, 35) are hereby not or only nimimally brought into operation due to respective arrangement and dimensioning of the catch members. The ancillary connections (34, 35) are only activated in the case of a further pressure increase due to overload or failure of the main connections (31, 32, 33).

9 Claims, 1 Drawing Sheet

IMPLANTABLE INFUSION PUMP

The invention concerns an implantable infusion pump for dosed emission of medicines into the human body according to the preamble of claim 1.

An implantable infusion of this kind is known from the DE 39 15 251 A1. This infusion pump comprises a pump chamber formed by a bowl-shaped lower chamber portion and an upper chamber portion connected thereto. The pump chamber in separated into two sectional chambers by a flexible membrane. A first sectional chamber is defined by the upper chamber portion and the membrane and formed as a medicine reservoir. The upper chamber portion comprises a refill aperture sealed by a pierceable septum. The septum is clamped between a septum holder connected to the upper chamber portion and the upper chamber portion. The medicine reservoir is connected to an outlet catheter by an outlet aperture and, if desired, an outlet reducer weans. A second chamber section is defined by the lower chamber portion and the membrane and serves as a pressure chamber for receiving a motive substance which expands at body temperature.

Similar infusion pumps of principally like construction are also known from the U.S. Pat. No. 3,731,681, the DE-OS 26 04 113 A1 and the U.S. Pat. No. 4,820,273.

The pump components of these infusion pumps are made of body-compatible metal alloys or plastics connected by welds or simple catch connections.

Such infusion pumps are used for continuous medication in patients who can otherwise only be medicated by means of injection of medicines several times a day.

The implantable infusion pump is thereby disposed in a subcutaneous bag in the area of the abdomen, whereby the refill aperture closed by the septum is touchable under the skin of the patient. The medicine reservoir is filled by injecting a syringe with a suitable cannula through the skin of the patient and the septum, and the medicine flows through the cannula into the medicine reservoir due to syringe pressure.

Such implantable infusion pumps must meet very high safety requirements. In the case of an infusion pump burst due to disconnection of individual components or of leaks on the connection points, uncontrolled flow of the medicine into the body of the patient results. Depending on the medicine administered, such overdosage can lead to a high health risk.

The connections inserted between the pump components must therefore retain their sealing function for a long implantation period of up to ten years. Improper filling of the medicine reservoir may, however, cause major pressure to develop. Whilst the operating pressure under normal conditions, depending on the motive substance, is between 0.6 bar and 2.5 bar above atmospheric pressure, in the case of improper filling, the internal pressures in the infusion pump can be up to 6.5 bar above atmospheric pressure. This results in considerable overstrain, particularly of the component connections, giving rise to the threat of disconnection or leakage and the attendant risks for the patient referred to above.

The problem of the invention is to provide a connection for components of an implantable infusion pump which is safer in the case of internal pressure overstrain.

The problem is solved by the characterising features of claim 1.

The principal and ancillary connections are preferably made by catch connection using catch members.

A further catch connection acting as an ancillary connection and comprising a reserve catch is thus provided for a catch connection acting as the main connection. This reserve catch connection engages smoothly and elastically if, under overstrain and pressure increase in the pump, structurally caused component deformation and component dislocation or a failure of the main connection occur.

The connection of pump components is hereby made more secure against total dissolution of the connection and leakages under overpressure. The risks for the patient are reduced correspondingly. In a preferred embodiment the infusion pump is formed as a disc-shaped body made of plastic and having rounded disc edges. The catch connections consist of concentrically disposed circumferential annular slots and associated annular bars or catch hooks. Such an embodiment is easy to manufacture and the required component elasticities can be well controlled. The refill aperture is preferably centered in a manner per se known and the septum is formed as a disc-shaped central septum. A concentric annular slot on whose inner and outer lateral wall catch slots are respectively arranged is molded in the upper chamber portion. The septum holder is arranged as a ring overlapping the edges of the central septum and comprises two annular bars flexibly disposed in parallel and extending into the annular slot, which respectively engage by latches with the catch slots of the annular slot. The two connections on the two catch slots represent a main connection and an associated ancillary connection, whereby the outer catch connection preferably forms the main connection.

In a particularly preferred embodiment an annular slot is provided on the upper inner edge area of the bowl-shaped bottom chamber portion, into which, in a catch connection forming the main connection, a circumferential associated edge of the upper chamber portion together with an O-ring and the edge of the membrane can be locked. On the outer lateral edge area a further annular slot is provided into which, in a catch connection forming an associated ancillary connection, a latch arrangement, suitably formed as a circumferential catch bar of an annular overlap part, engages. The oevrlap part thereby overlaps the upper chamber portion and the outer lateral edge area of the lower chamber portion in bell form and is supported by the upper chamber portion. The lower chamber portion and the upper chamber portion are hereby securely connected by a further component in the form of an overlap part in case of over-pressure. This overlap part can preferably further be used to form a covered annulus for inclusion of the outlet reducer means and the outlet catheter connection.

An annular chamber covered and sealed by an annular septum is preferably disposed on the outer wall of the upper chamber. The inner edge of the annular septum is covered and locked by the outer edge of the annular septum holder part, whilst the annular outer edge of the annular septum is covered and locked by an edge area of the overlap part. In this edge area of the overlap part a catch connection between the overlap part and the upper chamber portion is provided in the form of a catch slot and spring-elastic catch bars having latches engaging with the catch slot. A circumferential catch slot is suitably used on the overlap part and a circumferential latch on the upper chamber portion. This catch connection represents a main connection particularly for locking and sealing the annular septum. The above-described catch connection between the bottom chamber portion and the overlap part forms the associated ancillary connection.

Further details, features and advantages of the invention are shown in the following description of an exemplary embodiment by reference to the drawing.

The sole FIGURE shows a vertical section of an implantable infusion pump according to the invention.

FIG. 1 shows an implantable infusion pump 1 according to the invention for dosed emission of medicines into the human body. Infusion pump 1 is a disc-shaped rotation-symmetrical body made of plastic and comprises a housing consisting of a bowl-shaped lower chamber portion 2, a bowl-shaped upper chamber portion 3 of inverse curvature, an overlap part 4 and a septum holder 5 The interior is divided by a flexible membrane 6 into a first sectional chamber forming the medicine reservoir 7 and a second sectional chamber forming pressure chamber 8 for accomodation of a motive substance.

An annular slot 9 is molded in the upper inner edge area of the lower chamber portion 2. A circumferential associated upper edge 10 of the upper chamber portion 3 is caught and kept in sealed state in said annular slot 9 together with an O-ring 11 and an edge 36 of the membrane 6.

A refill aperture 12 is hermetically covered by a disc-shaped and pierceable central septum 13, whereby the refill aperture 12 comprises a refill chamber under the central septum 13 with a solid plate acting as the needle stop and passage openings to medicine reservoir 7.

A concentric annular chamber 14 hermetically covered by an annular septum 15 is further molded in the upper side of the upper chamber portion 3.

A concentric annular slot 16 to whose inner and outer lateral wall circumferential catch slots 17, 18 are respectively attached, is formed between the annular chamber 14 and the refill aperture 12. With its inner edge the annular septum holder 5 overlaps the edge of the disc-shaped central septum and with its outer edge it overlaps the inner annular edge of the ring septum 15. In addition, septum holder 5 engages in annular slot 16 with parallel annular bars 19, 20, whereby latches 21, 22 on annular bars 19, 20 engage in catch slots 17, 18.

The outer annular edge of the annular septum 15 is covered and securely sealed against upper chamber portion 3 in a stepped arrangement by a correspondingly formed edge area of the overlap part 4. For this purpose, a catch connection between the overlap part 4 and the upper chamber portion 3 consisting of a circumferential catch slot 23 on the overlap part 4 and a circumferential latch 24 on the upper chamber portion 3 is provided in this edge area of the overlap part 4.

On the lateral outer edge area of the lower chamber portion 2 a further annular slot 25 is molded, into which a circumferential latch 26 engages together with an inserted O-ring 27. The latch 26 represents the lower edge of the overlap part 4, whereby said overlap part 4 overlaps the lateral area of the upper chamber portion 3 and the outer lateral edge area of the lower chamber portion 2 in bell-shaped arrangement. The overlap part 4 is supported (under high pressure strain) by the upper chamber portion 3 by means of the latch arrangement 24 and by means of annular septum 15 by the lower chamber portion 2.

Between the outer wall area of the upper chamber portion 3 and an inner wall area of the overlap part 4 an annulus 28 for inclusion of an outlet reducer means 29 (shown here schematically as a section through a capillary) and of an outlet catheter 30 is formed.

The connection 31 formed by annular slot 9, edge 10 and O-ring 11 and the connection 32 formed by catch slot 23 and latch 24 as well as connection 33 comprising catch slot 18 and latches 22 represent main connections, which substantially accomodate the interior pressure strain occurring under normal operation.

Connection 34 consisting of annular slot 25, latch 26 and O-ring 27 as well as connection 35 comprising catch slot 17 and latches 21 are ancillary connections, which have no or only a minimal support function under normal operation. Only if the pressure rises above normal operating pressure, in particular in the case of failure of the main connections 31, 32 and 33, the anicillary connections 34 and 35 take over the support function.

The main connections 31, 32 and 33 are in permanent engagement and ensure the intregrity of the implanted infusion pump under normal operating conditions. If the interior pressure in either annulus 28 or the medicine reservoir 7 rises, the ancillary connections 34, 35 increasingly come into engagement. Hereby the tensions are abducted from the main connections 31, 32 and 33 and divide themselves between the main and the ancillary connections.

Should main connection 31, for example, fail, the connection function is taken over by ancillary connection 34. Since a gap between the upper chamber portion 3 and the lower chamber portion 2 is simultaneously generated, medicine escapes into the annulus 28 between the overlap part 4 and the upper chamber portion 3, so that the pressure and hence the strain on the connection as a whole is reduced. The ancillary connection 34 is hereby enabled to secure the integrity of the infusion pump against the environment. It is hereby essential that the lower portion fails in the upper bar area and not in the lower one, which can, however, be constructionally ensured.

If the main connection 32 between the upper chamber portion 3 and the overlap part 4 fails, the connection function is also taken over by ancillary connection 34.

In the case of failure or overload of the main connection 33, partial or complete takeover of the connection function by ancillary connection 34 occurs correspondingly In every case, the advantage of the invention is that, in case of overload or failure of the main connections 31, 32, 33, ancillary connections 34 and 35 are available which guarantee continued safe operation of the infusion pump 1, whereby the safety for the patient is substantially improved.

We claim:

1. Implantable infusion pump for dosed emission of medicines into the human body, comprising a pump chamber formed by a lower chamber portion and an upper chamber portion connected thereto, whereby the pump chamber is separated by a flexible membrane into two sectional chambers, of which the first sectional chamber is defined by the upper chamber portion and the membrane and is formed as the medicine reservoir, the upper chamber portion comprises a refill aperture sealed by at least one pierceable septum which is locked between a septum holder part connected to the upper chamber portion and the upper chamber portion, the medicine reservoir is connected through an outlet aperture and an outlet reducer means with an outlet catheter and the second sectional chamber is defined by the lower chamber portion and the membrane and is formed as a pressure chamber to accommodate a motive substance, and wherein internal pressure strain is generated under normal operating load; the infusion pump comprising:

the lower chamber portion and the upper chamber portion being in engagement by at least two associated connections, one of which being a main connection located proximal to said chambers and the other of which being an ancillary connection located distal to said chambers whereby the the main connection substantially supports the infusion pump against said internal pressure strain generated under normal operating load and, in the case of deformation of the lower chamber portion, the upper chamber portion and the septum holder part or slippage between the upper chamber portion and the lower chamber portion caused by a pressure increase above normal operating pressure and in the case of failure or deflection of the main connection, the ancillary connection is subjected to corresponding stress and supports the infusion pump against the pressure overload.

2. Implantable infusion pump according to claim 1, wherein at least two connections are formed by catch members as catch connections.

3. Implantable infusion pump according to claim 2, wherein the infusion pump is formed as a disc-shaped body with rounded disc edges and made of plastic and the catch connections are formed as main and ancillary connections with concentric annular catch slots engaged by associated latches carried by annular bars.

4. Implantable infusion pump according to claim 3, wherein the refill aperture is centered and the septum is a disc-shaped central septum, a concentric annular slot to whose inner and outer lateral wall circumferential catch slots are respectively attached is molded onto the upper chamber portion, the septum holder part is formed as a ring which overlaps the edges of the central septum and comprises two parallel annular bars which extend into the annular slot and respectively engage with the catch slots of annular slot by latches, whereby the two connections on both catch slots form a main connection and an associated ancillary connection.

5. Implantable infusion pump according to claim 4, wherein the connection on the outer catch slot forms the main connection and the connection on the inner catch slot forms the ancillary connection.

6. Implantable infusion pump according to claim 5, wherein on the upper inner edge area of the disc-shaped lower chamber portion an annular slot is provided, into which a circumferential associated edge of the upper chamber portion is clamped together with an O-ring and the edge of the membrane in a catch connection forming a main connection, on the outer lateral edge area of the lower chamber portion a further annular slot is provided, into which a latch arrangement of an annular overlap part engages in a catch connection formed as an associated ancillary connection, whereby the overlap part overlaps the upper chamber portion and the outer lateral edge area of the lower chamber portion in bell-shape arrangement and finds support on the upper chamber portion.

7. Implantable infusion pump according to claim 6, wherein an annulus is formed between an outer wall area of the upper chamber portion and an inner wall area of the overlap part.

8. Implantable infusion pump according to claim 7, wherein the annulus is formed to accommodate the outlet reducer means and the outlet catheter.

9. Implantable infusion pump according to claim 8, wherein an annulus surrounding the annular slot is formed on the outer wall of the upper chamber portion, and said annulus is covered and sealed by an annular septum, the edge of the annular septum pointing to the annular slot is covered and clamped by an outer edge of the annular septum holder member, the outer edge of the ring of the annular septum is covered and clamped by an edge area of the overlap part, and in this edge area of the overlap part a catch connection between the overlap part and the upper chamber portion comprising a catch slot and catch bars having circumferential latches engaging into said catch slot is provided, preferably a catch slot on the overlap part and a circumferential latch on the upper chamber portion, and this catch connection represents a main connection and the catch connection between the lower chamber portion and the overlap part represents an associated ancillary connection.

\* \* \* \* \*